United States Patent
Zeng et al.

(10) Patent No.: US 12,270,064 B2
(45) Date of Patent: Apr. 8, 2025

(54) PEPTIDE FOR COMPLEXING ZINC ION, COMPLEX THEREOF AND USE THEREFOR

(71) Applicant: Guangzhou University, Guangdong (CN)

(72) Inventors: Qingzhu Zeng, Guangdong (CN); Yingmin Zheng, Guangdong (CN); Qingling Xu, Guangdong (CN)

(73) Assignee: GUANZHOU UNIVERISTY, Guangdong (CN)

( * ) Notice: Subject to any disclaimer, the term of this patent is extended or adjusted under 35 U.S.C. 154(b) by 572 days.

(21) Appl. No.: 17/586,774

(22) Filed: Jan. 27, 2022

(65) Prior Publication Data

US 2022/0154239 A1    May 19, 2022

Related U.S. Application Data

(63) Continuation of application No. PCT/CN2020/117329, filed on Sep. 24, 2020.

(30) Foreign Application Priority Data

Jan. 22, 2020   (CN) .............................. 202010073635

(51) Int. Cl.
  *C12P 21/06*   (2006.01)
  *A23J 1/14*   (2006.01)
  *A23K 10/12*   (2016.01)
  *A23K 20/147*   (2016.01)
  *A23L 11/50*   (2021.01)

(52) U.S. Cl.
  CPC ............... *C12P 21/06* (2013.01); *A23J 1/148* (2013.01); *A23K 10/12* (2016.05); *A23K 20/147* (2016.05); *A23L 11/50* (2021.01)

(58) Field of Classification Search
  CPC ....... C12P 21/06; A23K 20/147; A23K 10/12; A23L 11/50
  See application file for complete search history.

(56) References Cited

FOREIGN PATENT DOCUMENTS

| CN | 101283805 A | 10/2008 |
|----|-------------|---------|
| CN | 103667407 A | 3/2014 |
| CN | 106260602 A | 1/2017 |
| CN | 107156856 A | 9/2017 |
| CN | 108201137 A | 6/2018 |
| CN | 108251488 A | 7/2018 |
| CN | 108531532 A | 9/2018 |
| CN | 109439715 A | 3/2019 |
| CN | 109957592 A | 7/2019 |
| CN | 111066963 A | 4/2020 |
| CN | 111253468 A | 6/2020 |

OTHER PUBLICATIONS

Machine translation of CN 111066963 A, accessed Oct. 10, 2024, pp. 1-7.*
Zheng, Ying-Min et al., Preparation Process Optimization of Soy Pedtides-Zinc Chelate and Its Structural Characterization, Science and Technology of Food Industry, 2020, pp. 160-165, No. 14, Abstract only.
Gao, Suyun, Preparation and Physiological Activity of Zinc Chelated Salts of Soybean Polypeptides, Full-text Database of China Outstanding Master's Thesis-Engineering Science and Technology (Series I), Mar. 15, 2004, pp. 24-48, Abstract only.
International Search Report of PCT Patent Application No. PCT/CN2020/117329 issued on Dec. 31, 2020.

* cited by examiner

*Primary Examiner* — Li N Komatsu
(74) *Attorney, Agent, or Firm* — LOZA & LOZA, LLP; Michael F. Fedrick

(57) ABSTRACT

The invention provides a peptide for complexing zinc ion, complex thereof and use therefor. The amino acid composition and sequence of the peptide for complexing zinc ion are Lys-Tyr-Lys-Arg-Gln-Arg-Trp (SEQ ID NO: 1). The peptide for complexing is derived from soybean or peanut, is an inherent component of foods, and has a super strong complexing effect with zinc ions.

9 Claims, 5 Drawing Sheets

Specification includes a Sequence Listing.

PEPTIDE FOR COMPLEXING ZINC ION, COMPLEX THEREOF AND USE THEREFOR

CROSS REFERENCE TO RELATED APPLICATIONS

The present application is a Continuation Application of PCT Application No. PCT/CN2020/117329 filed on Sep. 24, 2020, which claims the benefit of Chinese Patent Application No. 202010073635.X filed on Jan. 22, 2020. All the above are hereby incorporated by reference in their entirety.

REFERENCE TO SEQUENCE LISTING

A sequence listing is submitted as an ASCII formatted text filed via EFS-Web, with a file name of "Sequence_listing.TXT", a creation date of Jan. 27, 2022, and a size of 486 bytes. The sequence listing filed via EFS-Web is part of the specification and is incorporated in its entirety by reference herein.

TECHNICAL FIELD

The invention relates to the technical field of biochemical engineering, in particular to a peptide for complexing zinc ion, complex thereof and use therefor.

BACKGROUND

In China, the phenomenon of zinc deficiency is commonly seen among the crowd, and it is especially serious for children. Up to 39.6% of the children have different degrees of zinc deficiency, and the zinc deficiency rate is as high as 64.6% especially for children aged 3 to 4. For those aged 0 to 18, zinc deficiency ranks the first in trace element deficiencies with a zinc deficiency rate of 50% or more. Promoting the transport and absorption of the trace element zinc in the human body, and improving the absorption and the utilization rate of zinc are important scientific issues that have always been concerned with in the fields of food nutrition or functional foods. In addition, in order to avoid the crisis of illness caused by zinc deficiency in farmed livestock, poultry and aquatic animals, and so on, it is usually necessary to add zinc supplements to the feed. At present, inorganic zinc such as zinc oxide, zinc sulfate or zinc gluconate etc. is usually used as a zinc supplement for human or animal bodies.

Existing studies have found that it is organic zinc rather than inorganic zinc that actually plays a role inside the body. Organic zinc is closer to the functional form of zinc inside the organism, which can prevent the formation of insoluble substances inside the organism due to the supplement of inorganic zinc. Moreover, organic zinc has a higher biological efficiency than that of inorganic zinc, and only a trace amount of organic zinc is necessary to achieve the effect of zinc supplementation, which avoids the harm caused by excessive zinc inside the body due to poor absorption of inorganic zinc. Studies have shown that active peptides that have affinity with zinc ions ($Zn^{2+}$), peptides for complexing zinc, and their complexes can both promote the transport and the absorption of zinc. Peptide-zinc complex belongs to the category of organic zinc, is a new type of trace element enhancer that promotes the body's zinc intake, and is more helpful to promote the transport and the absorption of zinc by the body's cells.

At present, there is a general lack of related products of peptides for complexing zinc and complexes thereof in the market. Safe and effective organic zinc supplement products are lacked especially in aspects of foods and animal feed. Therefore, providing a stable and effective peptide for complexing zinc ion and its complexes can make up for the gap in this field.

SUMMARY OF THE INVENTION

The purpose of the present invention is to provide a peptide for complexing zinc ion, the complex thereof and use therefor.

The technical solutions used in the present invention are:
A first aspect of the present invention provides:
a peptide for complexing zinc ion having an amino acid composition and sequence of SEQ ID NO:1: Lys-Tyr-Lys-Arg-Gln-Arg-Trp (KYKRQRW).

In some embodiments, the above-described peptide for complexing zinc ion is derived from soybean, peanut or chemical synthesis. Certainly, other alternative amino acid and protein synthesis methods in this field can be reasonably selected according to actual needs, to obtain the above-mentioned peptide for complexing zinc ion.

A second aspect of the present invention provides:
a method for preparing a peptide for complexing zinc ion comprises steps as follows:
(1) taking soybean or peanut materials, and adjusting temperature and pH to perform enzymolysis, to obtain a protein peptide solution; and
(2) taking the protein peptide solution obtained in step (1), and subjecting it to separating, screening, and purifying, to obtain a peptide component, wherein the enzyme used for the enzymolysis is one or more selected from the group consisting of ALCALASE protease enzyme extract, papain and *Bacillus subtilis* neutral protease; and the peptide component contains the above-described peptide for complexing zinc ion.

Certainly, the preparation steps thereof can be reasonably increased or simplified according to actual needs, to obtain peptides with the same effect as the above-mentioned peptide component.

In some embodiments, the molecular weight of the peptide component in step (2) is 1 to 5 K Da; the content of Peptide is 15.58% to 17.18%; and the complexing rate of the zinc ion is 48.5% to 52.16%. Certainly, the molecular weight of the peptide component, the content of Peptide, and the complexing rate of the zinc ion can be reasonably selected according to actual needs.

In some embodiments, the way for the above-described separating, screening, and purifying in step (2) is one or more selected from the group consisting of ultrafiltration fractionation, gel chromatography and high performance liquid chromatography.

Certainly, other alternative means for separating, screening, and purifying in this field can also be reasonably selected according to actual needs.

In some embodiments, in step (1), the temperature is 35° C. to 55° C., and the pH is 6.0 to 8.5.

Certainly, the pH can be adjusted adaptively during selecting enzymes according to actual needs. Specifically, pH for the ALCALASE protease enzyme extract is 7.0 to 8.5, pH for the papain is 6.5 to 7.5, and pH for the *Bacillus subtilis* neutral protease is 6.0 to 7.0.

Certainly, other alternative enzymes in this field can also be reasonably selected according to actual needs.

A third aspect of the present invention provides:
a zinc ion complex, the preparation method thereof is:
taking the above-described peptide for complexing zinc ion or the above-described peptide component, adding a zinc ion solution, and adjusting the pH and the temperature to allow complete reaction.

Certainly, the preparation steps can be reasonably increased or simplified according to actual needs, to obtain a zinc peptide product having the same effect as the above-mentioned zinc ion complex.

In some embodiments, in the preparation reaction of the above-described zinc ion complex, the pH is 5.0 to 6.5, and the reaction temperature is 60° C. to 90° C.

Certainly, the pH and the temperature in the reaction can be adjusted reasonably according to actual needs.

In some embodiments, the above-described zinc ion solution is selected from the group consisting of zinc chloride solution, zinc sulfate solution, zinc oxide solution or zinc acetate solution; and the concentration in the solution is 0.1 to 1.0 mmol/L.

Certainly, other alternative solutions containing zinc ions with different concentrations can be reasonably selected according to actual needs.

A fourth aspect of the present invention provides:
uses of the above-described peptide for complexing zinc ion, the peptide component prepared by the above-described method, and the zinc ion complex in preparing foods and animal feed.

The beneficial effects of the present invention are:
1. the present invention provides a peptide for complexing zinc ion and its complex, and the amino acid composition and the amino acid sequence of the peptide are identified, which promotes the development of its directed synthesis and preparation process, and further produce the peptide-zinc complex in bulk; and
2. the peptide for complexing in the present invention is derived from soybean protein or peanut protein, which is an inherent component of food protein and has a super strong complexing effect with zinc ions.

DETAILED DESCRIPTION

In order to make the purpose, technical solutions and technical effects of the present invention clearer, the present invention will be further described in detail below in conjunction with specific embodiments. It should be understood that the specific embodiments described in this specification are only for explaining the present invention, not for limiting the present invention.

The following examples all use the same peptide for complexing zinc ion, and its amino acid composition and amino acid sequence are Lys-Tyr-Lys-Arg-Gln-Arg-Trp (SEQ ID NO: 1).

TABLE 1

Comparison of complexing rates of zinc of peptide segments with different molecular weights

| Items | Protein peptide solution | Peptide component SPIH1 | Peptide component SPIH2 | Peptide component SPIH3 | Peptide component SPIH4 |
|---|---|---|---|---|---|
| Molecular weight cut off (Da) | / | >5K | 1 to 5K | 0.5 to 1K | <0.5K |
| Content of Peptide (%) | / | 37.85 ± 1.98 | 16.38 ± 0.80 | 17.59 ± 0.55 | 28.16 ± 0.6 |
| complexing rate of zinc (%) | 30.96 ± 1.52$^c$ | 36.95 ± 3.62$^b$ | 50.33 ± 1.83$^a$ | 36.84 ± 3.14$^b$ | 10.31 ± 0.19$^d$ |

Significant difference coefficient p<0.05.

Example 1

Figure 1:
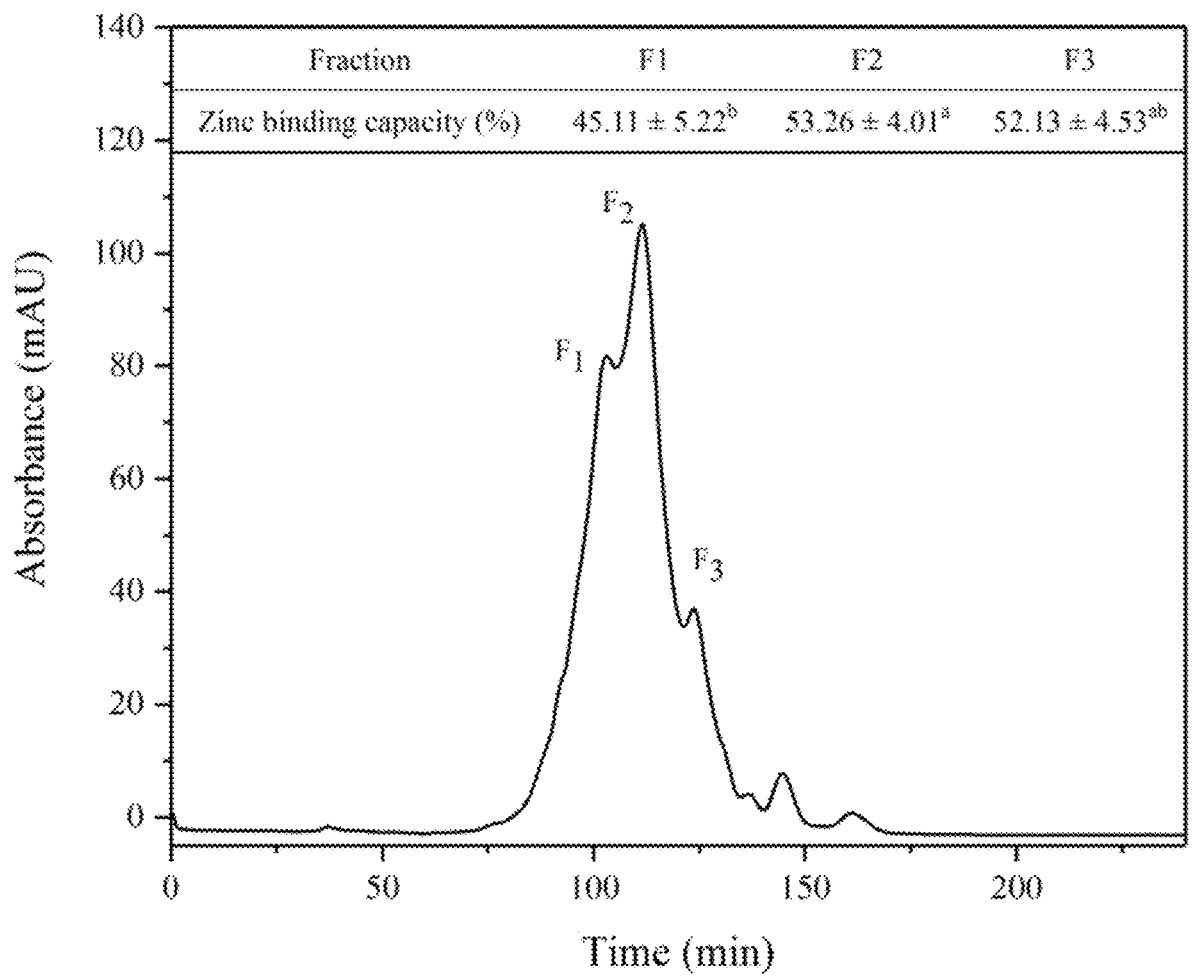
FIG. 1 is a gel chromatography separation spectrogram of the peptide component SPIH2.
Figure 2:
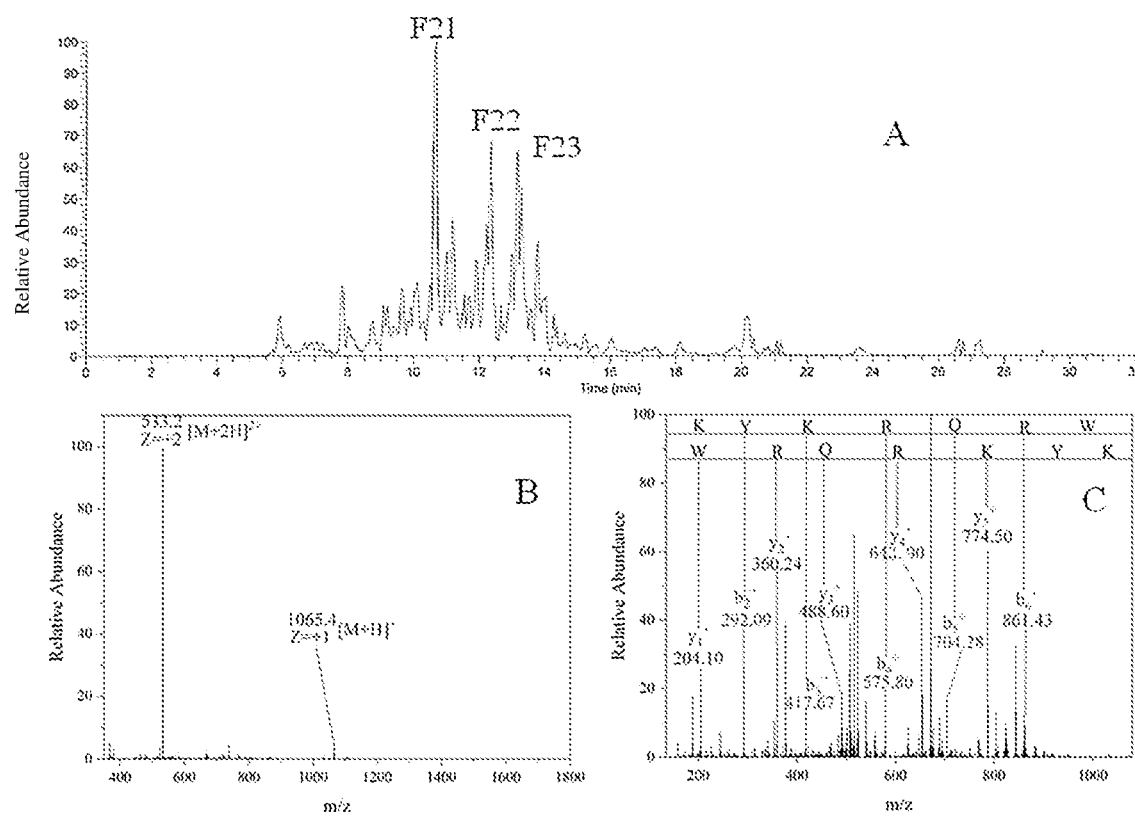
FIG. 2 is a sequence diagram of the amino acid composition of peptide for complexing F21 identified by HPLC (A) and LC-ESI/MS (B, C) methods.
Figure 3:
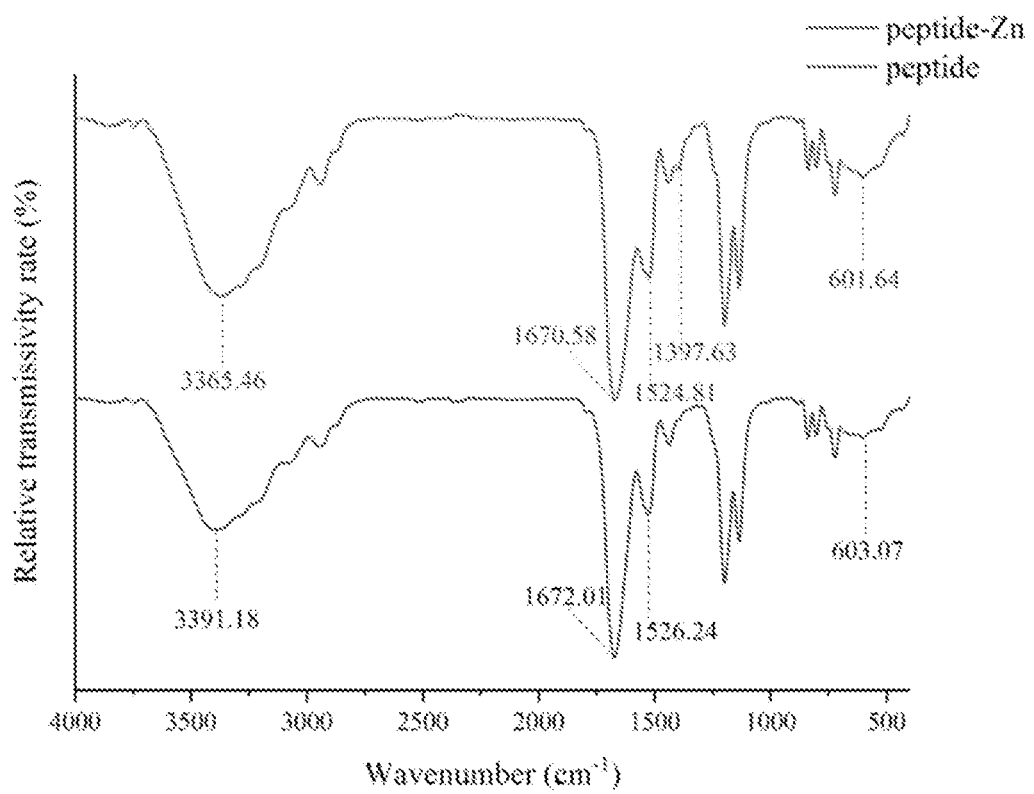
FIG. 3 is a comparison chart of infrared spectrum FTIR of peptide for complexing zinc ion and peptide-zinc complex.
Figure 4:
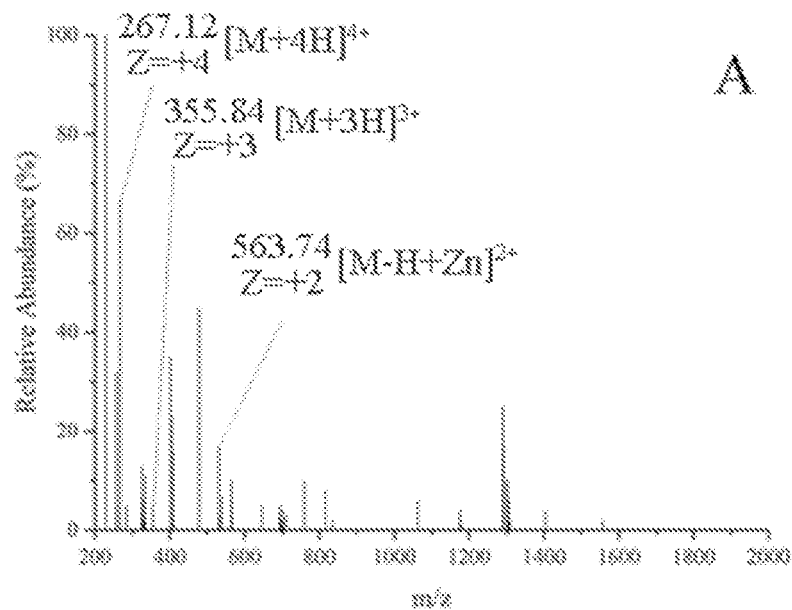
FIG. 4 is the first-order mass spectrum (A) and the second-order mass spectrum (B) for electrospray of the peptide-zinc complex.
Figure 4:
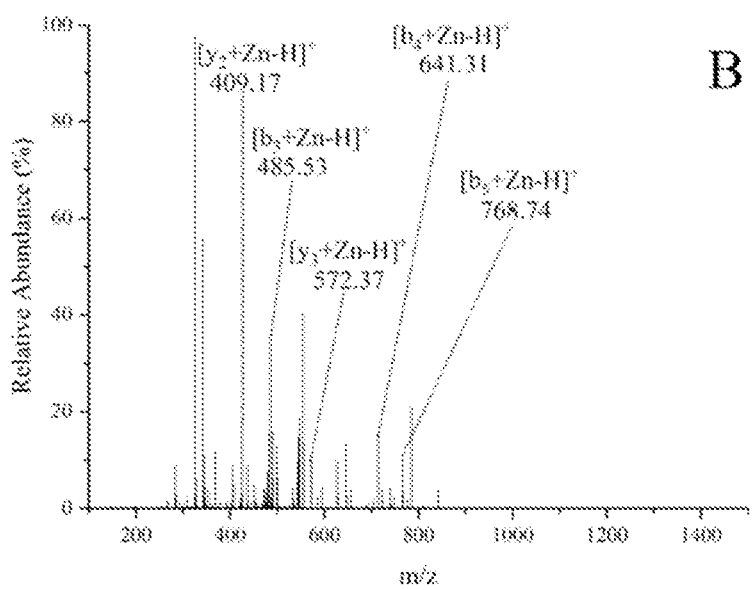
Figure 5:
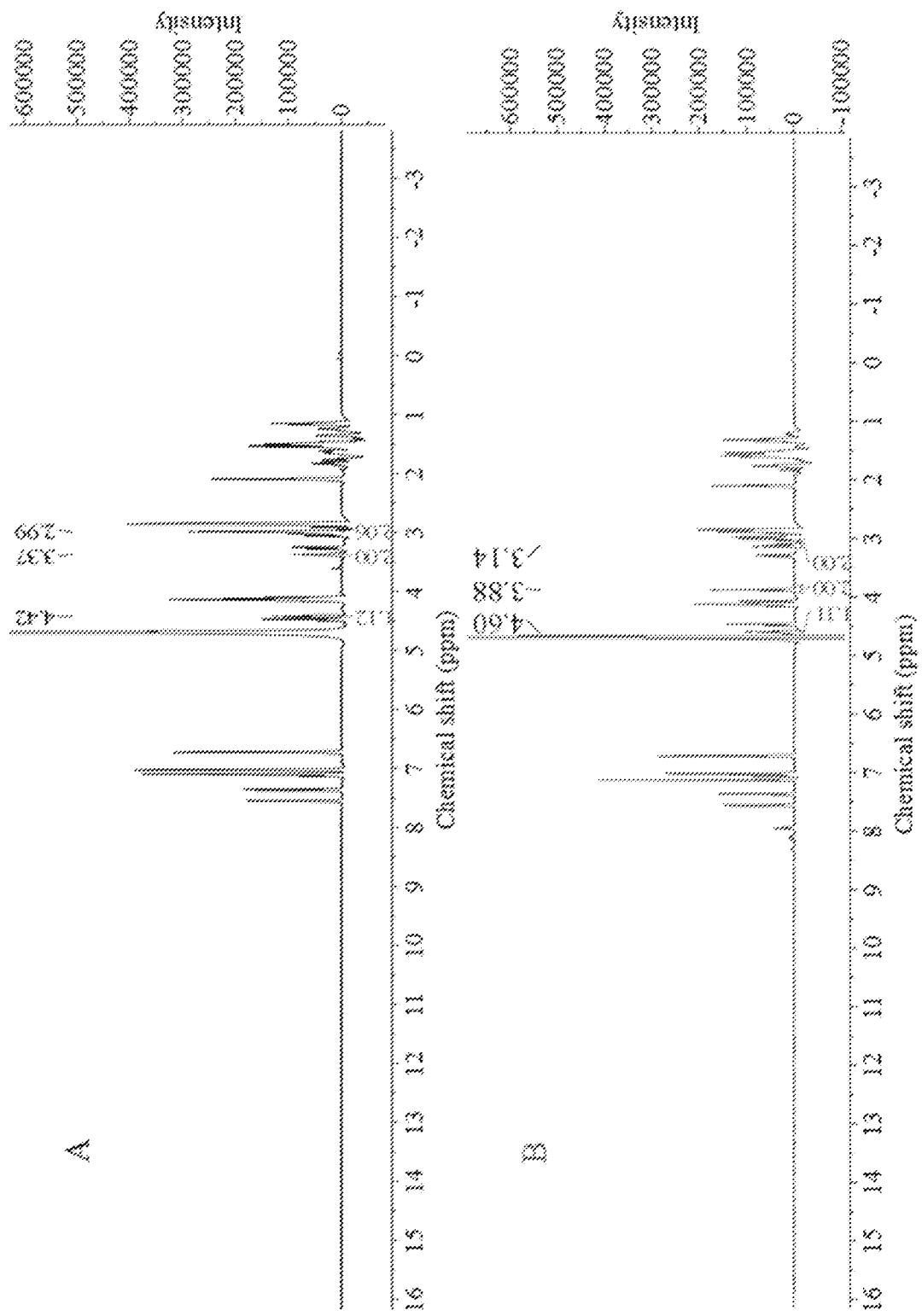
FIG. 5 is H-NMR spectra of the peptide for complexing zinc ion (A) and the peptide-zinc complex (B).

This example provides a method for preparing a zinc ion complex, and the steps include: (1) Mixing soybean protein powder with pure water in a ratio of 1:50, adjusting the temperature to 50° C. and the pH value to 8.0, and adding ALCALASE protease enzyme extract for enzymolysis;
(2) Taking the enzymatic hydrolysate obtained in step (1) for inactivating the enzyme at 100° C. for 5 minutes, centrifuging, and taking the supernate to obtain a protein peptide solution;
(3) Taking the protein peptide solution obtained in step (2) for ultrafiltering and fractionating, wherein the molecular weight cut offs of the ultrafiltration membrane are 5K Da, 1K Da, and 0.5K Da, respectively; and collecting the 1 to 5K Da peptide component SPIH2 with the strongest complexing rate of the zinc ion (see Table 1);
(4) Taking the SPIH2 component obtained in step (3) for gel chromatography separation, screening and collecting the peptide component F2 with the strongest complexing ability with zinc ions (see FIG. 1);
(5) Taking the peptide component F2 for separation and purification by high performance liquid chromatography (HPLC), to obtain the single peptide component for complexing F21 with the strongest complexing ability with zinc ion, and then using LC-ESI/MS for amino acid sequence analysis to identify the amino acid sequence of the peptide for complexing to be Lys-Tyr-Lys-Arg-Gln-Arg-Trp (i.e. KYKRQRW (SEQ ID NO: 1)) (see FIG. 2); and (6) Under conditions of a KYKRQRW (SEQ ID NO: 1) peptide concentration of 1 mg/mL, a zinc chloride $ZnCl_2$ concentration of 0.5 mmol/L, a reaction temperature of 70° C., and pH=5.5, subjecting the peptide for complexing (KYKRQRW (SEQ ID NO: 1)) and zinc ions to complexing reaction so as to generate peptide-zinc complex (KYKRQRW (SEQ ID NO: 1)-Zn) (see FIG. 3, FIG. 4, and FIG. 5).

Example 2

This example provides a method for preparing a zinc ion complex, and the steps include:
(1) Taking soybean meal for ultra-fine crushing or puffing followed by crushing to prepare soybean meal protein powder, then mixing soybean protein powder with pure water in a ratio of 1:10, adjusting the temperature to 50° C. and pH value to 7.0, and adding Papain and *Bacillus subtilis* neutral protease in sequence for enzymolysis;
(2) Taking the enzymatic hydrolysate obtained in step (1) for inactivating the enzyme at 100° C. for 5 minutes, centrifuging, and taking the supernate to obtain a protein peptide solution;
(3) Taking the protein peptide solution obtained in step (2) for ultrafiltering and fractionating, wherein the molecular weight cut offs of the ultrafiltration membrane are 5K Da, 1K Da, and 0.5K Da, respectively; and collecting the 1 to 5K Da peptide component SPIH2 with the strongest complexing rate of the zinc ion (see Table 1);
(4) Taking the SPIH2 component obtained in step (3) for gel chromatography separation, screening and collecting the peptide component F2 with the strongest complexing ability with zinc ions (see FIG. 1);
(5) Subjecting the peptide component F2 to separation and purification by high performance liquid chromatography (HPLC), to obtain the single peptide component for complexing F21 with the strongest complexing ability with zinc ion, and then using LC-ESI/MS for amino acid sequence analysis, to identify the amino acid sequence of the peptide for complexing to be Lys-Tyr-Lys-Arg-Gln-Arg-Trp (i.e. KYKRQRW (SEQ ID NO: 1)) (see FIG. 2); and
(6) Under conditions of a KYKRQRW (SEQ ID NO: 1) peptide concentration of 1 mg/mL, a zinc chloride $ZnCl_2$ concentration of 0.5 mmol/L, a reaction temperature of 70° C., and pH=5.5, subjecting the peptide for complexing (KYKRQRW (SEQ ID NO: 1)) and zinc ions to complexing reaction so as to generate peptide-zinc complex (KYKRQRW (SEQ ID NO: 1)-Zn) (see FIG. 3, FIG. 4, and FIG. 5).

Example 3

This example provides a preparation method and use of a zinc ion complex, and the steps include:
(1) According to the amino acid composition and sequence of the peptide for complexing zinc ion, using a solid phase peptide synthesis method to prepare a peptide for complexing zinc ion (Lys-Tyr-Lys-Arg-Gln-Arg-Trp) with a purity of 95% or more (see FIG. 2); and
(2) Preparing a peptide for complexing zinc ion (100 μM), dissolving it in a 50 mM phosphate buffer solution (pH 7.2) containing $ZnCl_2$ (250 μM), and stirring the mixture at room temperature to equilibrate for 1 hour; using a semi-permeable membrane with a molecular weight cut-off of 500 Da for dialysis for 5 hours to remove unbound zinc, collecting the retentate (complex), and freeze-drying to prepare the peptide-zinc complex powder.

The above-mentioned examples are preferred embodiments of the present invention, but the embodiments of the present invention are not limited by the above-mentioned examples, and any other changes, modifications, substitutions, combinations, and simplifications made without departing from the spirit and principle of the present invention should all be equivalent replacement modes, and they are all included in the protection scope of the present invention.

The invention claimed is:

1. A method of preparing a zinc ion complex, the method comprising:
   providing a peptide for complexing zinc ion, wherein the peptide consists of the amino acid sequence of SEQ ID NO: 1;
   adding a zinc ion solution to the peptide; and
   adjusting pH and temperature to allow complete reaction between the peptide and the zinc ion solution, to obtain the zinc ion complex.

2. The method according to claim 1, wherein the pH is 5.0 to 6.5, and the temperature is 60° C. to 90° C.

3. The method according to claim 1, wherein the zinc ion solution is zinc acetate solution, and the concentration of the zinc ion in the solution is 0.1 mmol/L to 1.0 mmol/L.

4. The method according to claim 1, wherein the peptide is derived from soybean.

5. A method of preparing a zinc ion complex, the method comprising the following steps:

(1) taking soybean materials, and adjusting temperature and pH to perform enzymolysis of the soybean materials with a protease, to obtain a mixture of protein and peptide solution;
(2) subjecting the mixture of protein and peptide solution to separating, screening, or purifying, to obtain a peptide component, wherein the peptide component comprises a peptide for complexing zinc ion, and wherein the peptide for complexing zinc ion consists of the amino acid sequence of SEQ ID NO: 1; and
(3) adding a zinc ion solution to the peptide component, and adjusting pH and temperature to allow complete reaction between the peptide component and the zinc ion solution, to obtain the zinc ion complex.

6. The method according to claim 5, wherein in step (3), the pH is 5.0 to 6.5, and the temperature is 60° C. to 90° C.

7. The method according to claim 5, wherein the zinc ion solution is zinc acetate solution, and the concentration of the zinc ion in the solution is 0.1 mmol/L to 1.0 mmol/L.

8. The method according to claim 5, wherein the step of separating, screening, or purifying in step (2) is one or more selected from the group consisting of ultrafiltration fractionation, gel chromatography and high performance liquid chromatography.

9. The method according to claim 5, wherein in step (1), the temperature is 35° C. to 55° C., and the pH is 6.0 to 8.5.

* * * * *

SEQUENCE LISTING

```
<160> NUMBER OF SEQ ID NOS: 1

<210> SEQ ID NO 1
<211> LENGTH: 7
<212> TYPE: PRT
<213> ORGANISM: Artificial Sequence
<220> FEATURE:
<223> OTHER INFORMATION: Synthetic

<400> SEQUENCE: 1

Lys Tyr Lys Arg Gln Arg Trp
1               5
```